United States Patent [19]

Peterson et al.

[11] Patent Number: 5,645,427
[45] Date of Patent: Jul. 8, 1997

[54] DENTAL IMPLANT MILLING TOOL AND METHODS OF THE USE THEREOF

[75] Inventors: Thomas S. Peterson, Lynn, Mass.; Dirk Schwichtenberg, Lage, Germany

[73] Assignee: North Shore Dental Porcelains Laboratories, Inc., Lynn, Mass.

[21] Appl. No.: 397,632

[22] Filed: Mar. 2, 1995

[51] Int. Cl.$^6$ .................................................. A61C 8/00
[52] U.S. Cl. ........................................ 433/173; 433/165
[58] Field of Search .............................. 433/165, 102, 433/166, 172, 173; 408/214, 223, 224, 225, 189

[56] References Cited

U.S. PATENT DOCUMENTS

| | | | |
|---|---|---|---|
| 332,308 | 12/1885 | Valentine | 408/223 |
| 1,070,425 | 8/1913 | Darling, Jr. | 408/224 |
| 3,346,894 | 10/1967 | Lemelson | 408/224 |
| 3,579,831 | 5/1971 | Stevens et al. | 32/10 |
| 3,802,055 | 4/1974 | Jackson | 408/224 |
| 3,905,109 | 9/1975 | Cohen et al. | 32/10 |
| 4,065,817 | 1/1978 | Branemark et al. | 3/1 |
| 4,330,891 | 5/1982 | Branemark et al. | 3/1 |
| 4,416,629 | 11/1983 | Mozsary et al. | 433/174 |
| 4,431,416 | 2/1984 | Niznick | 433/174 |
| 4,439,152 | 3/1984 | Small | 433/173 |
| 4,466,796 | 8/1984 | Sandhaus | 433/173 |
| 4,486,178 | 12/1984 | Schulte | 433/173 |
| 4,531,915 | 7/1985 | Tatum, Jr. | 433/173 |
| 4,531,916 | 7/1985 | Scantlebury et al. | 433/173 |
| 5,269,686 | 12/1993 | James | 433/174 |
| 5,312,253 | 5/1994 | Chalifoux | 433/173 |
| 5,312,255 | 5/1994 | Bauer | 433/174 |
| 5,312,256 | 5/1994 | Scortecci | 433/174 |
| 5,316,476 | 5/1994 | Krauser | 433/173 |
| 5,328,371 | 7/1994 | Hund et al. | 433/173 |
| 5,342,199 | 8/1994 | Gillespie | 433/173 |
| 5,344,457 | 9/1994 | Pilliar et al. | 623/16 |
| 5,350,300 | 9/1994 | Gallias | 433/173 |
| 5,366,374 | 11/1994 | Vlassis | 433/165 |
| 5,376,004 | 12/1994 | Mena | 433/173 |

FOREIGN PATENT DOCUMENTS 203866  9/1923  United Kingdom .................. 408/223

OTHER PUBLICATIONS

Predecki et al., *J. Biomed. Mater. Res.*, vol. 6, pp. 401–412 (1972).
Williams, Journal of Med. Eng. and Tech., pp. 266–270 (1977).
Beder et al., O.S., O.M. & O.P., pp. 787–799 (1959).
Branemark, *Scan. J. Plas. Recon. Surg.*, Vol. 11, Supp. 16p, p.7–132 (1977).

*Primary Examiner*—Cary E. O'Connor
*Attorney, Agent, or Firm*—Ernest V. Linek; Robert L. Buchanan

[57] ABSTRACT

Disclosed is a tool with cutting surfaces on the sides, end and tip that is inserted into a handpiece or milling machine. It is used according to a specific technique disclosed herein to mill precision surfaces in dental prostheses that are retained by screws to dental implants, abutments or replicas. The invention mills all types of dental implant prostheses that use a screw for retention. The milling tool of this invention allows the screw to pass through the screw access opening in the prosthesis and fit flush against the screw seat in the prosthesis, leaving space between the axial surfaces of the head of the screw and the screw access channel of the restoration. It also mills the small opening through the prosthesis through which the shank of the screw passes, so there is no contact between the prosthesis and the shank of the screw. It is important to not have contact between either the shank of the screw or the axial surface of the head of the screw with the prosthesis to avoid adverse tension of the screw. It maximizes optimal surface contact between the head of the screw and the prosthesis.

2 Claims, 1 Drawing Sheet

DENTAL IMPLANT MILLING TOOL AND METHODS OF THE USE THEREOF

BACKGROUND OF THE INVENTION

The present invention relates to the field of dentistry, particularly the dental implant field. This invention is important because since two-stage dental implants were introduced to the U.S. market in 1982, their use and popularity have soared. Implants of this type are described in many issued patents, including inter alia, U.S. Pat. Nos. 5,376,004; 5,366,374; 5,350,300; 5,344,457; 5,342,199; 5,328,371; 5,316,476; 5,312,256; 5,312,255; 5,312,253; 5,269,686, the disclosures of which are hereby incorporated herein by reference.

Other patents and publications describing known implant systems include the following; Schulte, U.S. Pat. No. 4,486,178; Scantlebury et al., U.S. Pat. No. 4,531,916; Tatum, Jr., U.S. Pat. No. 4,531,915; Sandhaus, U.S. Pat. No. 4,466,796; Small, U.S. Pat. No. 4,439,152; Niznick, U.S. Pat. No. 4,431,416; Mozsary et al., U.S. Pat. No. 4,416,629; Branemark et al., U.S. Pat. No. 4,330,891; Branemark et al., U.S. Pat. No. 4,065,817; Cohen et al., U.S. Pat. No. 3,905,109; Stevens et al., U.S. Pat. No. 3,579,831; Predecki et al., *J. Biotaed. Mater. Res.*, 6:401 (1972); Williams, J. Med. Eng. Tech., 266 (1977); Beder et al., *O.S.,O.M. & O.P.*, 787 (1959); Branemark et al., "Osseointegrated Implants in the Treatment of the Edentulous Jaw", *Scan. J. Plas. Recon. Surg.*, Vol. 11, Suppl. 16, (1977).

The most popular types of dental implant restorations are held in place by screws that thread into the implant or implant extension (abutment). One problem that has been discussed in dental meetings and in the scientific literature is the problem of screws that loosen up over time. Patients run the risk of having their prostheses and even implants destroyed because of this problem.

Pre-machined components (cylinders) have been developed by the manufacturers of dental implants to be incorporated into the restoration fabricated by the dental laboratory to provide a precision interface between the implant or implant extension and the seat of the head of the screw.

During the normal process of fabrication employed by dental laboratories, the surface of the interface against which the head of the screw fits, becomes less precise because of the investing and casting procedures.

During investing or mold-making, small minute air bubbles may get trapped in the cylinder. These small voids may be replaced by molten metal during the casting process. Expansion of the investment may not be identical to the expansion of the precision cylinder which is expanding in the mold. This might allow a small gap within the mold which would enable molten metal to flow into, eliminating the precision surface. Other laboratory processes such as cleaning out the investment after casting, as well as finishing techniques and sandblasting can ruin the precision surface. It has been suggested in the scientific literature that the heat involved in the casting process is enough to change the surface and shape of the pre-machined cylinder.

These pre-machined components are relatively expensive and even when the laboratory notices a problem with the screw seat, it is likely to try to grind away the imperfections making the machined surface equally imprecise, but less perceptible.

These surfaces against which the screw fits are often extremely difficult to inspect. They are deep within the restoration where they are not readily seen. These precision surfaces are never-the-less extremely important in obtaining the proper preload tension of the screw. Making the surface of the restoration where the head of the screw seats perfectly flat and perpendicular to the long axis of the implant will put less stress on the screw and allow for more optimum preload. This will extend the life of the screw and it will effectively solve many problems of screw-loosening.

A need was seen by the present inventor to develop a tool together with a technique for using that tool, that any laboratory could use with any type of dental implant system, to precisely mill the seat for the screw that holds the dental prostheses to the dental implant (or implant extension) to eliminate inaccuracies that occur in everyday fabrication processes in the dental laboratory.

Another important aspect of milling the screw seat pursuant to the teachings of this invention is to mill the opening through the center of the cylinder so the shaft of the screw does not contact as it passes through the restoration. If the shaft of the screw achieved contact on the axial walls of either the head of the screw or the shaft, the screw would come under tension reducing the amount of optimum preload required to keep the screw tight.

For these reasons, there is a need to mill the sides of the restoration at and above the screw seat as well as the opening beneath the screw seat. This allows the screw to be tightened so the head of the screw contacts only the base of the restoration and not the sides of the restoration, and allows the shaft of the screw to pass through the restoration without adverse contact.

One manufacturer (Interpore) saw the need for improving the interface of both the screw seat and the implant or implant extension seat after casting procedures. They produced an instrument the laboratory could use to remill these surfaces after casting. These instruments were turned by hand into the casting surface removing bubbles and debris. These instruments provided absolutely no level of precision, however, because they could cut at any angle and there was no technical means by which they could mill at the precise angle necessary to create a seat for the screw that would be perpendicular to the axis of the implant. This is important to achieve because stress is placed on the screw when the seat is not at a right angle to the shaft of the screw.

Another problem with Interpore's device is the screw seat device they used was tapered rather than flat. The vast majority of dental implants use a pan-head type screw that requires a flat surface for the head of the screw to fit against.

Implant Innovation, Inc. (31), another dental implant manufacturer, also sells and markets an instrument for milling the screw channel for UCLA abutments. This is also a manual instrument that provides no accuracy in milling the screw seat as it is operator sensitive. As with the Interpore instrument, it does not mill a flat area for the pan-head type screw and cannot be used for other types of dental implant cylinders. It is not effective in milling the screw seat so it is at the right angle to the shaft of the screw and it offers no precision surface for the screw to seat against.

Similar tools are also sold and marketed by Vident, Calcitek, Lifecore Biomedical and Attachments International with the same drawbacks and limitations.

Steri-Oss sells and markets hand instruments that mill the screw seat as well as the screw channel for a flat headed screw. This manufacturer realizes the limitations of these tools and cautions users in their prosthetic manual that over use of their tools seriously jeopardize the integrity of the screw seat. This tool is used manually and lacks the precision necessary to mill the screw seat perfectly flat and perpendicular to the long axis of the implant.

To achieve the purpose of milling the screw seat flat and at the correct 90° angulation to the axis of the implant, as well as centering the tool over the implant or abutment to provide the clearance for the shaft of the screw and the head of the screw, an entire set of procedures have been developed that can be followed and used by any person with an appropriate milling instrument.

SUMMARY OF THE INVENTION

The present invention is a tool which can be placed in a milling unit and used to precisely mill the inner surfaces of screw-retained dental implant prostheses such that the screw head seats flush against the restoration and so that no other contacting surface is present between screw and the prosthesis, such as the axial walls of the screw head or the shaft of the screw.

The tool of the present invention can be used to mill any type of dental material used in the fabrication of a dental implant prosthesis such as metals, alloys, ceramics, composite or acrylic resin or any combination of these materials. By following the present technique, the tool is centered over the implant. The tool mills the sides of the channel for the screw through the restorative material until it reaches the predetermined depth of the restoration. The tool then mills the base of the restoration where the head of the screw will ultimately seat and mills the opening through which the shaft of the screw passes.

The tool consists of a shaft which can fit into the chuck of a milling machine or handpiece. It has cutting surfaces on the sides of the tool. It has cutting surfaces on the end of the tool. It has an extension at the center of the end of the tool to penetrate and mill a smaller diameter hole. It is designed to fit into a pre-fabricated implant component, but to be wider in diameter than the screw or pin that holds the component to the dental implant, abutment or replica.

DETAILED DESCRIPTION OF THE PREFERRED EMBODIMENTS

Figure 1:
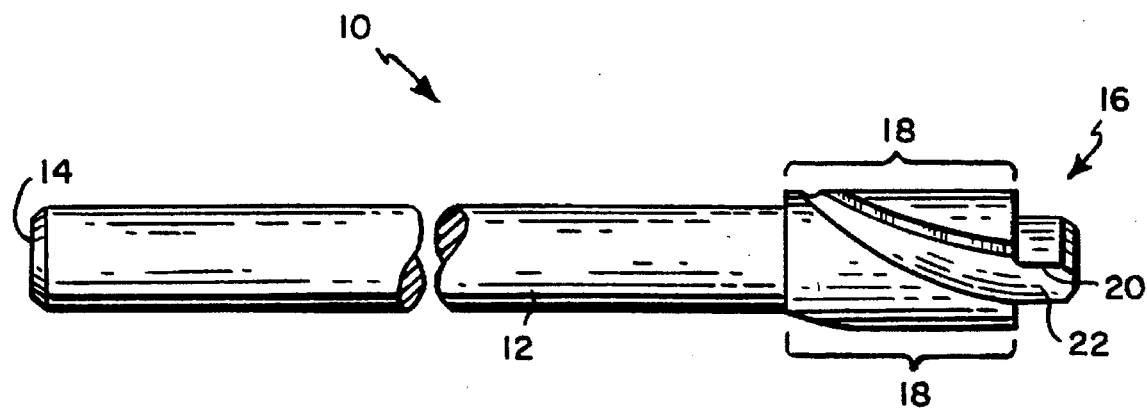
FIG. 1 is a side view of the milling tool of the present invention.
Figure 2:
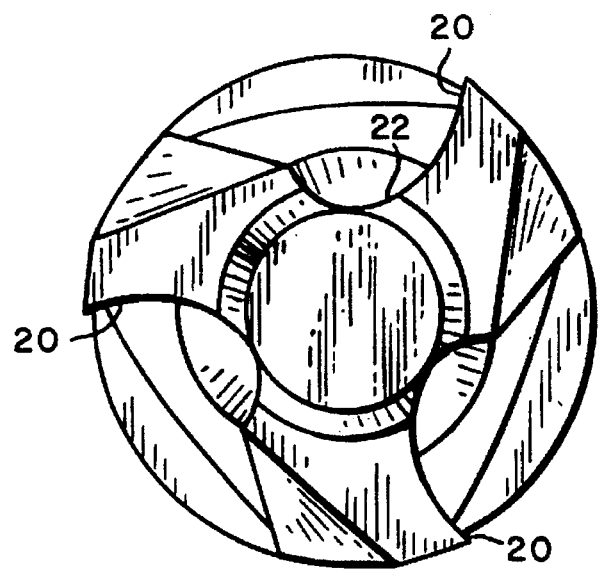
FIG. 2 is a cross-sectional view of the working end of the milling tool of the present invention.

As shown in FIGS. 1 and 2, the present invention comprises a tool (10) designed to mill the sides of the screw channel, the base of the screw channel (the screw seat) and the opening at the base of the screw channel, the screw shaft in screw-retained dental implant prostheses. The tool (10) consists of a shaft (12) which can fit at one end (14) into the chuck of a milling machine or handpiece. At the other end (16) the tool has cutting surfaces (18) provided on the sides of the tool. The tool (10) also has cutting surfaces (20) on the end of the tool. Finally, the tool (10) has an cutting extension (22) at the center of the end of the tool to penetrate and mill a smaller diameter hole. This is designed to fit into a pre-fabricated implant component, but to be wider in diameter than the screw or pin that holds the component to the dental implant, abutment or replica. The tool may be prepared from any materials useful for cutting, i.e., machining the metals commonly used for the manufacture of dental implants, i.e., titanium, titanium alloys, steels, steel alloys, etc. Useful materials are described in the patents cited herein.

To use the tool correctly, the tool must be positioned so that it is parallel to the long access of an implant replica or abutment replica that is used as a laboratory model of the patient. It must also be centered over the implant or abutment replicas.

It must therefore be used in a milling machine or drill that can be precisely positioned over the replicas on the working model so that the tool can be rotated at sufficient speed to mill the appropriate surfaces of the dental prosthesis. A milling machine is one such device widely used in the dental laboratory profession that accomplishes this task. In milling procedures, it is recommended to use duplicate models so the master model is at no risk of being damaged.

The first step then is to duplicate the position of the implant or abutment replicas. This is accomplished by attaching impression copings or pre-machined cylinders to the replicas on the master cast with long laboratory screws designed by the manufacturer of the dental implant system. These copings or cylinders are joined together with composite or acrylic resin. Shrinkage of this materials is compensated for by sectioning between the copings and using small amounts of the same material to rejoin the sectioned parts.

When this assembly is complete and fulfills the need of fitting the master model accurately, the laboratory screws are removed. The assembly is next removed from the master model. Individual implant or abutment replicas are attached to the assembly with screws. One long laboratory screw is used in at least one of the cylinders, if there are one or more cylinders present.

The milling machine is then prepared. One preferred milling machine is the Milling Machine F1, manufactured by Degussa of Frankfort, Germany, although any milling machine that meets the above requirements could be used.

The horizontal movement of the horizontal support beam is locked in position with the milling spindle approximately centered over the magnetic working plate so that only vertical movement of the horizontal support beam is permissible. The depth stop collar is rotated to allow sufficient movement of the spindle holder to be lowered by the lowering lever. This sufficient movement allowed should be equal or greater than height of the prosthesis to be milled.

The long laboratory screw that is attached to the assembly is inserted into the milling spindle. A plaster build-up dish large enough to accommodate all the implant or abutment replicas positioned on the assembly is placed beneath the assembly onto the magnetic working plate. The horizontal support beam is lowered to check that the plaster build-up dish is positioned to accept all of the replicas that are on the assembly.

Once the plaster build-up dish is positioned correctly, the magnet on the magnetic working plate is activated. The horizontal support beam is raised to allow room to fill the build-up dish with mounting stone. The preferred mounting stone used herein is Bitestone (Whip Mix, Louisville, Ky.) although any accurate fast-setting dental stone may be used. This particular stone was mixed according to the manufacturer's recommendations of 32 cc water to 100 g of powder for 30 seconds.

The stone is mixed and poured into the plaster build-up dish. A small amount of stone is painted onto the replicas on the assembly. The horizontal support beam is lowered until the replicas are fully seated into the stone mixture. After the stone has set, the long laboratory screw is released from the milling spindle and the horizontal support beam is raised.

The above described procedure has now accomplished two goals. One goal has been to line up the tool of this invention to the long axis of the implant replica. The other goal has been to center the tool of this invention over the long axis of the implant replica. Replacing the long laboratory screw with the present tool has centered the tool over the long axis of the implant and provided the exact perpendicular position to mill the screw seat at a 90° angle to the long axis.

The present tool is now inserted into the milling spindle. The assembly is removed from the newly made duplicate model. A new, unused cylinder from the manufacturer of the dental implant system is placed on the implant/abutment replica directly beneath the invention tool. This cylinder is placed passively without any screw to hold it in place.

The lowering lever is fully lowered and locked in place by the star grip. If the cylinder interferes with fully lowering the lowering lever, the horizontal support beam should be raised vertically to allow full lowering of the lowering lever. Once the lowering lever is locked in its most lowered position, the horizontal support beam is lowered until the invention tool is contacting the screw seat of the unused cylinder. The height stop collar is now brought up to contact the horizontal support beam and locked into place.

Through this process, another goal has been achieved. A definite vertical stop has been established according to the manufacturer of the dental implant cylinder. To mill less than the amount possible by lowering the horizontal support beam to the height stop collar and lowering the lowering lever so that the spindle holder bottoms out on the depth stop collar would not give us the depth into the restoration to achieve as much depth of the screw into the cylinder as the manufacturer has designed so that as many threads as designed reach into the dental implant. One also now can determine the maximum depth that can be milled in accordance with specifications provided by the manufacturer of this particular cylinder. The maximum and minimum drilling depths have been established by the previous procedure and the pre-machined cylinder.

Once the vertical drilling depth has been determined, the star grip is loosened to allow the lowering lever to be raised. The horizontal support beam is raised sufficiently to allow removal of the unused cylinder and replacement with the dental prosthesis to be milled. The dental prosthesis is held in place manually and the horizontal support beam is lowered until it bottoms out on the height stop collar.

Milling oil is liberally applied to the invention tool and rotation is set between 4500 and 5000 rpm and turned on. The lowering level is repeatedly lowered and raised as needed to successfully mill out imperfections caused by investing, casting and/or metal finishing errors. Milling oil is applied during this process to provide necessary cooling and lubrication. This milling procedure is carried out until the lowering lever is fully lowered as determined by contact between the spindle holder and the depth stop collar.

Because manufacturers of dental implant cylinders must produce large numbers of dental implant components, there exists a machining tolerance that allows measurable differences to exist among the components each manufacturer produces. For this reason it may be necessary to lower the drilling depth of the milling machine to mill the prosthesis so the screw seat is fully machined.

The prosthesis may be removed anytime during the milling process, inspected and re-positioned on the duplicate model with complete accuracy. Additional drilling depths may be accomplished by turning the depth stop collar in increments of approximately 0.01 mm in a clockwise direction until the surface is fully machined upon inspection.

In the case of a single-tooth prosthesis, the procedure has been completed. In the case of a prosthesis connected to multiple implants, additional milling procedures are required. In this case, the duplicate model is removed from the plaster build-up dish and trimmed on a model trimmer. The impression coping/cylinder assembly is repositioned on the duplicate model. This time a different cylinder is held in place by the long laboratory screw. The laboratory screw is inserted into the milling spindle. The plaster build-up dish is positioned so to hold the duplicate model. The duplicate is dropped into the wet stone that is placed into the plaster build-up dish and the entire procedure is again repeated until all of the cylinders are remilled according to the above protocol.

When the procedure described above is performed on all of the cylinders involved in retaining a dental implant prosthesis, each screw will be optimally positioned to gain the maximum surface area obtainable by tightening with the least amount of adverse force transmitted by contact with undesirable surface contact areas.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A method for joining a restoration to a dental implant comprising at least one screw-threaded cylinder, said method comprising:
    (a) aligning a milling tool comprising a two-ended shaft which can fit at one end into a chuck of a milling machine or handpiece; while at the other end the shaft has a plurality of cutting surfaces, wherein: one cutting surface is provided on the sides of the tool; another end cutting surface is provided on the face end of the tool; and another tip cutting surface is provided as an axial extension from the center of the shaft end; parallel to the long axis of a replica of an implant;
    (b) determining a vertical stop distance in the cylinder;
    (c) milling the restoration sufficiently to form a screw channel for a retaining screw comprising a shaft and a head, said milling being in line with the long axis of the replica and extending apically from the occlusal surface of the restoration to a distance about equal to the base of the head of the retaining screw;
    (d) milling the screw channel to form a seat for the head of the retaining screw; and
    (e) joining the restoration and the implant, wherein when the retaining screw is threadably engaged to the vertical stop distance, the head of the retaining screw seats flush against the base of the restoration, and the shalt and axial walls of the retaining screw are spaced from the cylinder and the restoration, respectively.

2. A method for joining a restoration to an implant extension comprising at least on screw-threaded cylinder said method comprising:
    (a) aligning a milling tool of comprising a two-ended shaft which can fit at one end into a chuck of a milling machine or handpiece; while at the other end the shaft has a plurality of cutting surfaces, wherein: one cutting surface is provided on the sides of the tool; another end cutting surface is provided on the face end of the tool; and another tip cutting surface is provided as an axial extension from the center of the shaft end; parallel to the long axis of a replica of the implant extension;
    (b) determining a vertical stop distance in the cylinder;

(c) milling the restoration sufficiently to form a screw channel for a retaining screw comprising a shaft and a head, said milling being in line with the long axis of the replica and extending apically from the occlusal surface of the restoration to a distance about equal to the base of the head of the retaining screw;

(d) milling the screw channel to form a seat for the head of the retaining screw; and (e) joining the restoration and the implant extension, wherein when the retaining screw is threadably engaged to the vertical stop distance, the head of the retaining screw seats flush against the base of the restoration, and the shall and axial walls of the retaining screw are spaced from the cylinder and the restoration, respectively.

* * * * *